United States Patent [19]
Mazo et al.

[11] Patent Number: 5,872,285
[45] Date of Patent: Feb. 16, 1999

[54] PRODUCTION OF D,L-ASPARTIC ACID

[75] Inventors: Grigory Ya Mazo; Jacob Mazo, both of Skokie; Barney Vallino, Jr., Naperville; Robert J. Ross, Elmhurst, all of Ill.

[73] Assignee: Donlar Corporation, Bedford Park, Ill.

[21] Appl. No.: 661,054

[22] Filed: Jun. 10, 1996

[51] Int. Cl.$^6$ .................... C07C 227/00; C07C 229/00
[52] U.S. Cl. .................................... 562/554; 526/571
[58] Field of Search ...................... 562/554, 571

[56] References Cited

U.S. PATENT DOCUMENTS

| | | | |
|---|---|---|---|
| 4,839,461 | 6/1989 | Boehmke et al. | 528/363 |
| 5,219,952 | 6/1993 | Koskan et al. | 525/419 |
| 5,292,858 | 3/1994 | Wood | 528/345 |
| 5,373,088 | 12/1994 | Koskan et al. | 528/363 |
| 5,491,213 | 2/1996 | Batzel | 528/480 |

FOREIGN PATENT DOCUMENTS

| | | | |
|---|---|---|---|
| 126075 | 6/1976 | German Dem. Rep. | |
| 2 029 502 | 6/1970 | Germany | 562/571 |
| 133691 | 1/1982 | Poland | |
| 143183 | 4/1984 | Poland | |

*Primary Examiner*—Frederick Krass
*Attorney, Agent, or Firm*—Olson & Hierl, Ltd.

[57] ABSTRACT

The present invention is directed to a method for the production of D,L-aspartic acid. The method comprises reacting an unsaturated dicarboxylic acid or anhydride, such as, maleic acid, fumaric acid, maleic anhydride, or mixtures thereof, with excess aqueous ammonia at an elevated temperature and pressure for a time sufficient to produce diammonium D,L-aspartate. The produced diammonium D,L-aspartate is then neutralized to D,L-aspartic acid. Excess unreacted ammonia and various by-products may be recycled and re-used in the method, thereby minimizing waste and reducing cost. The produced D,L-aspartic acid may be subsequently used to make polyaspartic acid.

24 Claims, 1 Drawing Sheet

PRODUCTION OF D,L-ASPARTIC ACID

FIELD OF THE INVENTION

The invention relates to a method for the production of D,L-aspartic acid.

BACKGROUND OF THE INVENTION

D,L-aspartic acid is useful for the production of polysuccinimide and polyaspartic acid. Poly-alpha,beta-D,L-aspartic acid, copolymers of poly-alpha,beta-D,L-aspartic acid, and their salts are generally water soluble, biodegradable polymers useful in a variety of applications. Such applications include detergent formulations, water treatment, oral hygiene products, pharmaceuticals, agricultural applications, oil production, cosmetics, and personal care products, such as hair and skin care products.

Polyaspartates can be manufactured by polymerization of D,L-aspartic acid and L-aspartic acid, or by polymerization of maleic acid in the presence of ammonia. The polyaspartates derived from D,L-aspartic acid and L-aspartic acid are generally useful in a wide variety of applications. Such applications include uses as mineral scale inhibitors in water treatment; scale and corrosion inhibitors in oil production; humectants in personal care products; and, nutrient absorption enhancers in agriculture. However, the polyaspartates derived from maleic acid and ammonia are not suitable for use in many applications due to limitations on molecular weight or color.

L-aspartic acid is the only form of aspartic acid which is currently available on a large commercial scale. L-aspartic acid is used in the manufacture of the artificial sweetener, aspartame. The manufacture of L-aspartic acid involves the use of fermentation or other biotechnology processes and can be expensive.

The production of D,L-aspartic acid by various methods is known in the art. Polish Pat. No. 133691 and Polish Pat. No. 143183 disclose the production of D,L-aspartic acid by reacting maleic acid and ammonia in the presence of a large amount of ammonium chloride at an elevated temperature and pressure. The resulting diammonium salt of aspartic acid is acidified with hydrochloric acid to afford a 60% yield of D,L-aspartic acid. However, for every mole of aspartic acid produced by the disclosed process, four moles of ammonium chloride are produced as waste. Inclusion of a large amount of ammonium chloride and the acidification with hydrochloric acid are undesirable process expedients because of the added waste produced, and because of the corrosive nature of such additives which requires special process equipment.

East German Pat. No. DD126075 discloses a method for the manufacture of D,L-aspartic acid in which maleic anhydride is neutralized with aqueous ammonia at a normal pressure and an elevated temperature. An additional solvent, N-formylacetamide, is added and the solution is heated at 120–130 degrees C. Hydrochloric acid is then added to the reaction mixture to yield D,L-aspartic acid. However, the N-formylacetamide is destroyed in this process, creating undue waste and added expense. Inclusion of an additional solvent, such as N-formylacetamide, in the method of the present invention would have a deleterious effect because of the added waste and expense. In addition, carrying out the method of the present invention at a normal, rather than an elevated pressure, would have an adverse effect on the formation of the reaction product.

U.S. Pat. No. 4,839,461 to Boehmke teaches the production of polyaspartic acid by reacting maleic acid and ammonia. The products can be converted into D,L-aspartic acid by treatment with hydrochloric acid. The process of Boehmke teaches the addition of a metal hydroxide or ammonium hydroxide, the reaction of maleic acid and ammonia in a molar ratio of 1:1–1.5, and the production of monoammonium salt.

In addition, methods of manufacturing polymers of aspartic acid are known. U.S. Pat. No. 5,219,952 to Koskan et al. teaches the production of high molecular weight polysuccinimide and high molecular weight polyaspartic acid from maleic anhydride and ammonia. U.S. Pat. No. 5,292,858 to Wood teaches the production of copolymers of polyamino acids. U.S. Pat. No. 5,373,088 to Koskan et al. teaches the production of polyaspartic acid from maleic acid and ammonia. U.S. Pat. No. 5,491,213 to Batzel teaches the production of polysuccinimide by reacting an unsaturated dicarboxylic acid or anhydride with a particulate ammonium salt.

The known methods for producing D,L-aspartic acid have several disadvantages. They are more costly because additional reactants and more expensive plant equipment must be used, thus increasing the cost. They are more wasteful because various end products and by-products are discarded rather than recycled back into the process.

Therefore a need exists for a more efficient and low-cost method of producing D,L-aspartic acid that simultaneously yields a high amount of product. The method of the present invention overcomes the problems associated with the known methods of making D,L-aspartic acid by recovering and recycling excess ammonia used in the method, as well as recovering and recycling various additional by-products for re-use in the method. Such recycling of products reduces waste and provides for a more efficient method of production. Thus, the present invention provides an efficient, cost-effective method for the manufacture of D,L-aspartic acid.

SUMMARY OF THE INVENTION

The present invention provides a method for producing D,L-aspartic acid directly from an unsaturated $C_4$ dicarboxylic acid or anhydride. The method comprises the steps of reacting an unsaturated dicarboxylic acid or anhydride which is a member of the group consisting of maleic acid, fumaric acid, maleic anhydride, and mixtures thereof, with excess aqueous ammonia, at an elevated temperature and pressure for a time period sufficient to produce diammonium D,L-aspartate; neutralizing the produced diammonium D,L-aspartate with an acid to produce D,L-aspartic acid; and thereafter, isolating the produced D,L-aspartic acid.

It is an aspect of the present invention to provide a method for producing D,L-aspartic acid, wherein the produced diammonium D,L-aspartate is neutralized with a mineral acid, such as hydrochloric acid, nitric acid, phosphoric acid, or sulfuric acid, to produce a reaction product containing D,L-aspartic acid.

It is another aspect of the present invention to provide a method for producing D,L-aspartic acid, wherein the produced diammonium D,L-aspartate is neutralized with an unsaturated dicarboxylic acid or anhydride, such as maleic acid, fumaric acid, maleic acid anhydride, or mixtures thereof, to produce a reaction product containing D,L-aspartic acid and a recyclable by-product which is a diammonium salt of the corresponding dicarboxylic acid. The recyclable by-product may be diammonium maleate or diammonium fumarate. The method may further include the steps of combining the diammonium maleate or diammonium fumarate by-product with aqueous ammonia and recycling the resulting admixture to the reacting step.

It is another aspect of the present invention to provide a method for producing D,L-aspartic acid, which further includes the steps of recovering an unreacted amount of the excess ammonia from the reaction of the unsaturated dicarboxylic acid or anhydride with the excess ammonia and recycling the unreacted ammonia to the reacting step.

The present invention therefore provides a method for producing D,L-aspartic acid directly from an unsaturated dicarboxylic acid or anhydride. Because various products in the method of the present invention are capable of being recycled and are not discarded as waste, the present invention is more efficient and less wasteful than other known methods. As a result of the reduced waste, the method is more cost-effective because only raw materials are fed in and only product is removed. Also, higher yield of D,L-aspartic acid may be obtained at a lower cost in this manner.

Other features and advantages of the present invention will be apparent upon reading the following detailed description of the invention and preferred embodiments of the invention.

DETAILED DESCRIPTION OF THE PREFERRED EMBODIMENTS

Figure 1:
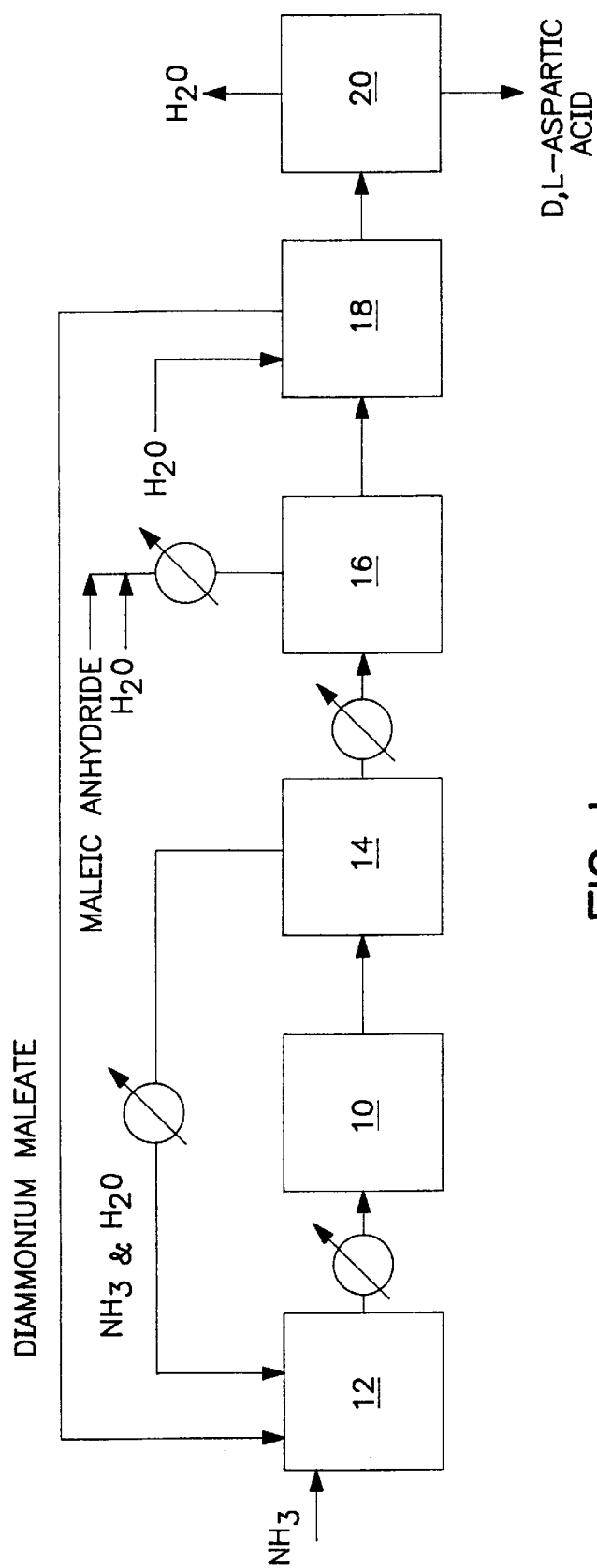
FIG. 1 is a schematic block diagram illustrating a continuous process embodiment of the present invention.

The present invention is susceptible of embodiments in various different forms. The specification describes in detail a preferred embodiment of the invention. It is to be understood that the present disclosure is to be considered as an exemplification of the principles of the invention. It is not intended to limit the broad aspects of the invention to the illustrated embodiment.

The term "about" as used herein with range specifications is meant to cover a range encompassing measurable tolerances.

The present invention provides a method for producing D,L-aspartic acid directly from an unsaturated dicarboxylic acid or anhydride. The method comprises the initial step of reacting an unsaturated dicarboxylic acid or anhydride with excess aqueous ammonia, at an elevated temperature and pressure for a time period sufficient to produce diammonium D,L-aspartate. The method further includes the steps of neutralizing the produced diammnonium D,L-aspartate with an acid to produce D,L-aspartic acid and the step of isolating the produced D,L-aspartic acid. Neutralization can be effected with a mineral acid, with an unsaturated dicarboxylic acid or its anhydride, or with carbon dioxide, the latter a precursor of carbonic acid which forms a solution of ammonium carbonate and/or ammonium bicarbonate.

Specifically, in the first step of the method of manufacture of D,L-aspartic acid, an unsaturated dicarboxylic acid or anhydride is combined and reacted with an excess amount of ammonia in an aqueous solution. The preferred unsaturated dicarboxylic acid or anhydride contemplated for use in the present invention includes maleic acid, fumaric acid, maleic anhydride, or mixtures thereof.

The molar ratio of the unsaturated dicarboxylic acid or anhydride to excess ammonia may be in the range of about 1:4 to about 1:50. It is preferred that the molar ratio of unsaturated dicarboxylic acid or anhydride to excess ammonia is in the range of about 1:8 to about 1:20. The concentration for the aqueous solution of unsaturated dicarboxylic acid or anhydride may preferably be in the range of about 5% (w/w) to about 50% (w/w).

The unsaturated dicarboxylic acid or anhydride and excess aqueous ammonia are reacted together in a suitable reaction vessel at an elevated temperature in the range of about 40 degrees C. to about 200 degrees C. For the purposes of this invention, by the term "elevated temperature" is meant a temperature above ambient temperature. The preferred temperature is in the range of about 80 degrees C. to about 180 degrees C.

The unsaturated dicarboxylic acid or anhydride and excess aqueous ammonia are reacted at an elevated pressure up to about 1500 psig. For the purposes of this invention, by the term "elevated pressure" is meant a pressure above ambient pressure. The preferred pressure range is from about 275 psig to about 1000 psig. The most preferred pressure range is about 300 psig to about 800 psig.

Typically, the period of time sufficient for reacting the unsaturated dicarboxylic acid or anhydride and the excess ammonia solution is in the range of about 30 minutes to about 5 hours.

The unsaturated dicarboxylic acid or anhydride and the excess aqueous ammonia are reacted at an elevated temperature and an elevated pressure for a sufficient period of time, to produce diammonium D,L-aspartate, also known as the diammonium salt of aspartic acid. Excess unreacted ammonia utilized in this initial reacting step is recovered from the reaction, such as by venting the reaction vessel at temperatures of about 40 degrees C. to about 100 degrees C. and condensing the ammonia, or by trapping the ammonia in a water scrubber. The recovered unreacted ammonia may then be re-used or recycled back to the reaction step.

The method of the present invention further includes a neutralization step. In the neutralization step, the resulting diammonium D,L-aspartate produced in the reaction step is neutralized with a suitable acid to precipitate D,L-aspartic acid. A preferred pH for neutralization is about 4 to about 1.5. Product recovery can be further enhanced by cooling the neutralized reaction mixture to a temperature below ambient, preferably, below about −5° C.

The diammonium D,L-aspartate may be neutralized with a mineral acid to produce 2 moles of ammonium salt for every 1 mole of D,L-aspartic acid produced. Mineral acids such as hydrochloric acid, sulfuric acid, or phosphoric acid, are preferred.

Alternatively and preferably, the diammonium D,L-aspartate may be neutralized with an unsaturated dicarboxylic acid or anhydride to produce 1 mole of diammonium maleate or diammonium fumarate for every 1 mole of aspartic acid produced. The more preferred unsaturated dicarboxylic acid or anhydride for neutralization includes maleic acid, fumaric acid, maleic anhydride, or mixtures thereof. The diammonium maleate or diammonium fumarate so produced may then be re-used or recycled in the method to produce additional D,L-aspartic acid. The recycling is accomplished by adding a sufficient amount of ammonia to the diammonium maleate or diammonium fumarate to satisfy the stoichiometry and provide for a slight excess to make up for losses, and reacting while heating the solution under elevated pressure as in the initial step of the method. The resulting admixture is then recycled back to the reacting step.

Upon neutralization, the D,L-aspartic acid forms a precipitate or crystallizes out as a solid. The D,L-aspartic acid is, in turn, isolated via filtration or centrifugation or other methods known in the art.

The method of the present invention may also be performed in a continuous manner, for example, by utilizing a flow-through pressure reactor. In such an event, an aqueous solution of an unsaturated $C_4$ aliphatic dicarboxylic acid, or mixtures thereof, and ammonia are pumped into one end of a reactor, which can be a heated tubular pressure vessel or the like, while withdrawing a mixture of reactants and reaction products from the other end of the reactor. The pressure in the reactor is maintained by a suitable pump at the reactor inlet and by a backpressure regulator at the reactor outlet. The pressure drop experienced by the process stream constituted by the mixture of reactants and reaction products as this stream exits the reactor promotes the evaporation of excess ammonia therefrom. The evaporated ammonia is then recovered, condensed, and recycled.

A continuous process embodiment is illustrated in FIG. 1 in which pressurized reactor 10 maintained at an appropriate reaction temperature receives a reactant admixture from feed tank 12. Upon exiting from reactor 10, the resulting mixture of reactants and reaction products is fed to flash vessel 14 where unreacted ammonia and approximately 20 weight percent of the water that is present flashes overhead and is returned to feed tank 12. Also added to the contents of feed tank 10 is make-up ammonia in an amount sufficient to maintain the molar ratio of dicarboxylic acid-to-ammonia within the range discussed hereinabove. The resulting, substantially ammonia-free liquid, containing the corresponding diammonium salt, is then fed from flash vessel 14 to precipitator 16 where D,L-aspartic acid is produced upon neutralization. For neutralization purposes an aqueous solution of an acid or an acid anhydride, e.g., maleic anhydride, is added to precipitator 16 so as to precipitate out the D,L-aspartic acid. The aspartic acid suspension produced in precipitator 16 is conveyed to centrifuge 18 for product separation and washing, followed by drying in drier 20. Dicarboxylic acid salts recovered in centrifuge 18 are recycled to feed tank 12. In the embodiment illustrated in FIG. 1 the dicarboxylic acid salt is diammonium maleate.

The following non-limiting examples are provided to illustrate the manufacture of D,L-aspartic acid by the method of the present invention:

EXAMPLE 1

Reaction vessel was a 0.33 liter autoclave which was charged with a saturated aqueous solution of ammonia (150 g) and diammonium maleate (30 g) at a temperature of about 25–40 degrees C. The autoclave was sealed and then pressurized through a gas inlet valve with ammonia gas to a constant pressure of about 114 psig for a period of 30 minutes. The gas inlet valve was then closed and the autoclave maintained at 40 degrees C. for 30 minutes. The autoclave was thereafter heated to about 140–150 degrees C. over a period of 40 minutes and maintained in this temperature range for an additional 50 minutes. The pressure within the reaction vessel rose from about 114 psig to about 700 psig during this heating period. After the temperature of about 140–150 degrees C. and the autogenous pressure had been maintained for 50 minutes, the contents of the reactor were expelled into a second vessel at ambient pressure. The resulting solution of diammonium D,L-aspartate was then neutralized while in the second vessel to a pH of 2.8 (isoelectric point of aspartic acid) with concentrated hydrochloric acid (about 12 molar). A white precipitate of D,L-aspartic acid formed within a few minutes of neutralization with the acid. The precipitated D,L-aspartic acid was isolated by filtration and dried to afford a 71% yield of white crystalline powder. The product was identical to an authentic sample of D,L-aspartic acid obtained by both NMR (Nuclear Magnetic Resonance) and IR (InfraRed) techniques.

EXAMPLES 2–9

Examples 2–9 were performed in a similar manner. The experimental results are compiled in TABLE I, below.

TABLE I

Synthesis of D,L-Aspartic Acid

| Ex. # | Diammonium Maleate (g) | Additional Ammonium Hydroxide, 29% w/w (g) | Ammonia Pressurization Time (min) | Reaction Temperature (°C.) | Reaction Time (h) | Pressure Maximum of Reaction (psig) | Yield as Free Acid on Isolation (%) | Acidification Method |
|---|---|---|---|---|---|---|---|---|
| 2 | 30 | 150 | 30 | 150 | 1.5 | 700 | 40 | conc. aqueous maleic acid, final pH 2.2, room temperature |
| 3 | 30 | 150 | 30 | 100 | 3 | 230 | 0 | N/A |
| 4 | 30 | 150 | none | 150 | 3 | 300 | 77 | conc. aqueous HCl, final pH 2.2, room temperature |
| 5 | 15 | 150 | none | 150 | 3 | 300 | 58 | conc. aqueous HCl, final pH 2.2, room temperature |
| 6 | 60 | 150 | none | 150 | 3 | 300 | 58 | conc. aqueous HCl, final pH 2 2 room temperature |
| 7 | 80 | 100 | nnne | 150 | 3 | 260 | 0 | N/A |
| 8 | 60 | 150 | none | 150 | 3 | 300 | 60 (from two separate isolations) | reaction solution split into two parts for workup; one was acidified with conc HCl (aq) to pH 2.8 at −2° C., other width solid maleic acid (1.00 equivalent) to same conditions; products are identical by IR, purity and yield |
| 9 | 45 | 150 | none | 180 | 1.5 | 450 | 38 | conc. aqueous HCl, final pH 2.8 at −2° C. |

It will be understood that the invention may be embodied in other specific forms by one of ordinary skill in the art without departing from its spirit or central characteristics. The foregoing examples and accompanying discussion are intended as illustrative, and are not intended to be limiting to the details of the listed embodiments. Rather, the invention is defined by the claims, and as broadly as the prior art will permit.

We claim:

1. A method for producing D,L-aspartic acid which comprises the steps of providing a separately prepared diammonium salt of an unsaturated $C_4$ aliphatic carboxylic acid;

combining said separately prepared diammonium salt of an unsaturated $C_4$ aliphatic dicarboxylic acid with a molar excess of aqueous ammonia so as to produce a reaction mixture;

maintaining said reaction mixture at an elevated temperature and pressure for a time period sufficient to produce diammonium D,L-aspartate;

adding to the produced diammonium D,L-aspartate a neutralizing acid to produce D,L-aspartic acid; and isolating the product D, L-aspartic acid.

2. The method in accordance with claim 1 wherein said dicarboxylic acid is maleic acid.

3. The method in accordance with claim 1 wherein said dicarboxylic acid is fumaric acid.

4. The method in accordance with claim 1 wherein said dicarboxylic acid is a mixture of maleic acid and fumaric acid.

5. The method in accordance with claim 1 wherein said diammonium salt of an unsaturated $C_4$ aliphatic dicarboxylic acid is diammonium maleate.

6. The method in accordance with claim 1 wherein said neutralizing acid is maleic acid.

7. The method in accordance with claim 1 wherein said neutralizing acid is a mixture of maleic acid and fumaric acid.

8. The method in accordance with claim 1 wherein said neutralizing acid is provided as malcic acid anhydride.

9. The method in accordance with claim 1 wherein said neutralizing acid is a mineral acid.

10. The method in accordance with claim 9 wherein the mineral acid is a member selected from the group consisting of hydrochloric acid, nitric acid, phosphoric acid, sulfuric acid, and mixtures thereof.

11. The method in accordance with claim 1 wherein the produced D,L-aspartic acid is isolated by filtration.

12. The method in accordance with claim 1 wherein the produced D,L-aspartic acid is isolated by centrifugation.

13. The method of claim 1 wherein the elevated temperature is in a range of about 40 degrees C. to about 200 degrees C.

14. The method of claim 1 wherein the elevated temperature is in a range of about 80 degrees C. to about 180 degrees C.

15. The method of claim 1 wherein the elevated pressure is in a range of about 275 psig to about 1000 psig.

16. The method of claim 1 wherein the elevated pressure is in a range of about 300 psig to about 800 psig.

17. The method of claim 1 wherein the time period is in a range of about 30 minutes to about 5 hours.

18. The method of claim 1 wherein the mole ratio of the diammonium salt to the excess aqueous ammonia is in the range of about 1:4 to about 1:50, respectively.

19. The method of claim 1 wherein the mole ratio of the diammonium salt to the excess ammonia is in the range of about 1:8 to about 1:20, respectively.

20. The method of claim 1 further including the steps of recovering unreacted excess ammonia and recycling the unreacted ammonia to the combining step.

21. The method of claim 1, wherein a recyclable by-product is produced upon addition of the neutralizing acid and is combined with the reaction mixture.

22. A method for producing D,L-aspartic acid directly from an unsaturated $C_4$ dicarboxylic acid or anhydride which comprises the steps of:

combining a separately prepared diammonium maleate with excess aqueous ammonia, in a mole ratio in the range of about 1:4 to about 1:50, respectively;

reacting the separately prepared diammonium maleate with said excess ammonia at an elevated temperature in a range of about 40 degrees C. to about 200 degrees C., at an elevated pressure in a range of about 275 psig to about 1000 psig, and for a time period of about 30 minutes to about 5 hours, to produce diammonium D,L-aspartate;

recovering unreacted excess ammonia and recycling the recovered unreacted ammonia to the reacting step;

neutralizing the produced diammonium D,L-aspartate with a mineral acid which is a member selected from the group consisting of hydrochloric acid, nitric acid, sulfuric acid, phosphoric acid, and mixtures thereof to produce a reaction product containing D,L-aspartic acid; and thereafter, isolating the D,L-aspartic acid.

23. The method in accordance with claim 1 wherein the neutralizing acid is an unsaturated dicarboxylic acid or anhydride thereof.

24. The method in accordance with claim 9 wherein the mineral acid is hydrochloric acid.

* * * * *